United States Patent [19]

Kroenke et al.

[11] 4,375,569

[45] Mar. 1, 1983

[54] PROCESS FOR THE OXYCHLORINATION OF AN ALKANE USING A SOLID SOLUTION CATALYST CONTAINING IRON CATIONS

[75] Inventors: William J. Kroenke, Brecksville; Paul P. Nicholas, Broadview Heights, both of Ohio

[73] Assignee: The B. F. Goodrich Company, Akron, Ohio

[21] Appl. No.: 950,119

[22] Filed: Oct. 10, 1978

Related U.S. Application Data

[60] Division of Ser. No. 741,910, Nov. 15, 1976, which is a continuation-in-part of Ser. No. 564,794, Apr. 3, 1975, abandoned.

[51] Int. Cl.³ ............................................ C07C 17/154
[52] U.S. Cl. .................................. 570/224; 570/243; 570/245; 585/658; 585/661
[58] Field of Search .......... 260/654 A, 656 R, 659 A; 585/658, 620, 624, 629, 661; 570/224, 243, 245

[56] References Cited

U.S. PATENT DOCUMENTS

| | | | |
|---|---|---|---|
| 2,838,577 | 6/1958 | Cook et al. | 260/656 |
| 3,420,901 | 1/1969 | Schulz | 260/659 |
| 3,629,354 | 12/1971 | Beard | 260/683.3 |
| 3,649,560 | 3/1972 | Croce et al. | 252/432 |
| 4,042,639 | 8/1977 | Gordon et al. | 260/656 R |
| 4,102,935 | 7/1978 | Kroenke et al. | 260/656 R |
| 4,102,936 | 7/1978 | Magistro | 260/656 R |

FOREIGN PATENT DOCUMENTS

1016495  1/1966  United Kingdom ........... 260/659 A

OTHER PUBLICATIONS

Technical Paper No. 10, *Alumina Properties*, Allen S. Russell (1953), Aluminum Company of America.

*Primary Examiner*—Charles F. Warren
*Assistant Examiner*—Joseph A. Boska
*Attorney, Agent, or Firm*—Alan A. Csontos; Joe A. Powell

[57] ABSTRACT

An alkane is reacted with oxygen and available chlorine in the presence of a solid solution catalyst containing iron cations to yield unsaturated hydrocarbons and chlorinated saturated and unsaturated hydrocarbons. In a preferred embodiment of the process, ethane is reacted with oxygen and available chlorine in the presence of a solid solution catalyst containing iron cations to yield vinyl chloride, ethylene, and other valuable by-products. The conversion of ethane to products approaches 100 percent, vinyl chloride is prepared in up to 40 mole percent yield, and the combined yield of vinyl chloride, ethylene dichloride, ethyl chloride, and ethylene is up to 90 mole percent.

3 Claims, No Drawings

PROCESS FOR THE OXYCHLORINATION OF AN ALKANE USING A SOLID SOLUTION CATALYST CONTAINING IRON CATIONS

CROSS REFERENCE TO RELATED APPLICATION

This is a division of application Ser. No. 741,910 filed filed on Nov. 15, 1976, which in turn is a continuation-in-part of Ser. No. 564,794 filed Apr. 3, 1975, now abandoned.

BACKGROUND OF THE INVENTION

The reaction of an alkane in the presence of a catalyst to form unsaturated hydrocarbons is well known. If a chlorine source is present, chlorinated saturated and unsaturated hydrocarbons are also produced. Perhaps the most familiar of such processes is the preparation of vinyl chloride.

Vinyl chloride ($CH_2=CHCl$) itself can be prepared using a number of different processes. Two familiar processes are (1) the hydrochlorination of acetylene and (2) the oxychlorination of ethylene to form dichloroethane which in turn is dehydrohalogenated to form vinyl chloride (see C. A. Schildknecht, *Vinyl and Related Polymers*, John Wiley and Sons, Inc., N.Y., N.Y. (1952), pages 388–390, and U.S. Pat. No. 2,847,483). As acetylene is more expensive than ethylene, the latter process is economically favored, and much activity is noted in this art area (see U.S. Pat. Nos. 3,634,330; 3,454,663; 3,448,057; and 3,624,170). Ethylene, in turn, can be prepared by the oxydehydrogenation of ethane (see U.S. Pat. No. 3,769,362). The processes have been combined so that vinyl chloride can be directly produced using ethane as a feed stock (see U.S. Pat. Nos. 2,838,577; 3,658,933; 3,658,934, and 3,551,506). It is the nature of the processes which use ethane as a feed stock to produce vinyl chloride and ethylene, along with other valuable products such as ethylene dichloride and ethyl chloride. As ethylene, ethylene dichloride, and ethyl chloride can be readily reacted to form more vinyl chloride, the processes are often rated and compared on their ability to yield all four products. However, high conversion of ethane to products and high yield of vinyl chloride is particularly desired.

The present invention is directed to an improved process for the oxychlorination of an alkane and particularly for the preparation of ethylene and vinyl chloride from ethane which process employs specific solid solution catalysts containing iron. The catalysts of the invention exhibit improved activity and longer lifetimes compared to conventional iron containing catalysts. Catalysts containing iron are known to the art; see U.S. Pat. Nos. 3,849,339; 3,769,362; 3,723,351; 3,703,593; 3,658,934; 3,658,933; 3,207,809; 2,847,483; and 2,674,633, U.S. Publication No. B 380,979, and British Patent No. 1,039,369. An article in the Journal of The American Ceramic Society, Vol. 43, No. 7 (1960), page 367, discloses compounds of lanthanum and iron and recently issued U.S. Pat. No. 3,904,553 discloses certain solid solutions as having activity as catalysts.

SUMMARY OF THE INVENTION

The invention comprises an improved catalyst and process for the oxychlorination of an alkane and particularly for the preparation of ethylene and vinyl chloride from ethane. The catalyst is a solid solution catalyst containing iron cations substituted for cations of a host lattice selected from the group consisting of $\alpha$-$Al_2O_3$, $\beta$-$Al_2O_3$, $Ba\,Al_{12}O_{19}$, $Ba_{0.50}Ce_{0.17}Ag_{0.33}Al_{12}O_{19}$, and $\alpha$-$Cr_2O_3$. Use of the novel catalysts in the process of the invention produces yields of up to 40 mole percent of vinyl chloride and up to 90 combined mole percent of vinyl chloride, ethylene, ethyl chloride, and ethylene dichloride. The catalysts can remain active for up to 100 hours without substantial loss of iron, and can then be readily reactivated by heating the catalyst to above about 1200° C.

DETAILED DESCRIPTION OF THE INVENTION

An alkane, such as ethane, is combined with oxygen and a chlorine source such as hydrogen chloride and is oxychlorinated in the presence of a solid solution catalyst of the invention to prepare unsaturated hydrocarbons, saturated chlorinated hydrocarbons, and unsaturated chlorinated hydrocarbons such as ethylene, ethyl dichloride, and vinyl chloride and other valuable by-products. Depending upon feed and reactor conditions, about 5 to 40 mole percent yield of unsaturated chlorinated hydrocarbon such as vinyl chloride and up to a 90 mole percent total yield of products such as vinyl chloride, ethylene dichloride, ethyl chloride, and ethylene can be obtained. Conversion of alkane to products can approach 100 mole percent.

The alkane that can be employed in the process of the invention can have 1 to about 12 or more carbon atoms. Examples of such alkanes are methane, ethane, propane, n-butane, t-butane, n-hexane, n-octane, isooctane, n-decane, and the like. More preferably, the alkane employed has 2 to about 6 carbon atoms, exemplified by ethane, propane, n-butane, and n-hexane. Most preferably, the alkane used in the process of the invention is ethane. Hereinafter, reference will be made to the use of ethane in the process, although it is understood that other alkanes can be likewise employed.

In the process, ethane, oxygen, and a chlorine source are placed into a reactor vessel containing the solid solution catalyst containing iron cations. The process contemplates the use of any standard technique for oxychlorination concerning the type of operation, reactor size and design, and the like. The process can be operated as a batch process, but is preferably conducted as a continuous process wherein reactants and products are continuously added and withdrawn. The solid solution catalyst can be supported or unsupported, and can be fixed as in a bed or present as particles that can readily fluidize during operation. A preferred process is to employ the solid solution catalyst in particulate form that will fluidize during operation of the process thereby establishing maximum contact with the reactants. Such processes are known as fluid bed processes, and the reactors designed for such are known as fluid bed reactors. A typical reactor is designed such that one or more gaseous reactants is introduced in the reactor at a point below the catalyst bed, and the gas pressurized through the bed, lifting and suspending the catalyst in the reactor volume. Other reactants can be added at appropriate levels above, below, or any point in the fluid catalyst bed. Normally, products are withdrawn from the top portion of the reactor above the fluid bed and collected or further treated as desired.

Although the process contemplates the use of known operating techniques and reaction conditions, certain conditions are herein stated as useful and practical. The reactants comprise ethane, oxygen (usually used in the form of air), and a chlorine source. The chlorine can be supplied as anhydrous hydrogen chloride or as a mixture of anhydrous chlorine and hydrogen chloride. Using one mole of ethane as a basis, the hydrogen chloride is used at from about 0.1 mole to about 10 moles or more. More preferably, the hydrogen chloride is used at a level of from about 0.5 mole to 5 moles per mole of ethane. In general, the use of a higher ratio of hydrogen chloride to ethane increases the yield of vinyl chloride and other chlorinated products and decreases the yield of ethylene. However, high levels of hydrogen chloride (above 5 moles) increase the amount of hydrogen chloride to recycle. Excellent yields of vinyl chloride have been obtained using about 2 to 4 moles of hydrogen chloride per mole of ethane.

Oxygen, preferably in the form of dry air, is used at from about 0.1 mole to about 1.5 moles of oxygen to one mole of ethane. A more preferred level is from about 0.5 mole to about 1 mole. The use of levels of oxygen of over about 1 mole results in increased production of polychlorinated products, but also increases production of carbon oxides. Excellent yields of vinyl chloride have been obtained using a level of oxygen of from about 0.7 mole to 1.0 mole per mole of ethane.

Ethane, oxygen, and hydrogen chloride are put into the reactor as reactants. Temperature of reaction range from about 400° C. to about 650° C., and more preferably from about 475° C. to about 600° C. Materials withdrawn from the reactor in the product stream comprise vinyl chloride, ethylene, chlorinated products such as ethylene dichloride and ethyl chloride, carbon oxides (CO and $CO_2$), water and unreacted ethane and hydrogen chloride. Another product found in the exit stream is iron, presumedly in the form of iron chlorides such as ferric chloride. The iron present in the product stream includes iron lost from the catalyst.

The improved feature of the oxychlorination process is the use of specific solid solution catalysts containing iron cations as the oxychlorination catalysts. The catalyst itself is a solid solution of iron cations in specific host lattice selected from the group consisting of $\alpha$-$Al_2O_3$, $\beta$-$Al_2O_3$, $BaAl_{12}O_{19}$, $Ba_{0.50}Ce_{0.17}Ag_{0.33}Al_{12}O_{19}$ and $\alpha$-$Cr_2O_3$. This is in contrast to most standard catalysts wherein an active ingredient such as cupric chloride or iron oxide is merely absorbed onto the surface of a support structure or material. The difference between the catalysts of the invention and other known catalysts can be distinguished in the physical state of the catalyst and in the activity of the catalyst.

A solid solution catalyst is a true solution wherein cations are substituted for host lattice ions in the catalyst structure. An X-ray diffraction pattern of a solid solution catalyst is characteristic of the diffraction pattern of the host lattice. For example, a solid solution catalyst of iron cations in $\alpha$-$Al_2O_3$ will exhibit an X-ray diffraction pattern characteristic of $\alpha$-$Al_2O_3$. In contrast, if iron in the form of $Fe_2O_3$ is merely absorbed onto $\alpha$-$Al_2O_3$, the X-ray diffraction pattern will show the presence of both $Fe_2O_3$ and $\alpha$-$Al_2O_3$.

A distinguishing feature of the solid solution catalysts, compared to impregnated catalysts, is in the increased retention of iron upon use. For example, a solid solution catalyst containing iron cations in an $\alpha$-$Al_2O_3$ host lattice used at a given set of reaction conditions lost about 15% by weight of its original iron content after about 100 hours of use. In contrast, a catalyst comprised of ferric oxide merely absorbed onto $\alpha$-$Al_2O_3$, operating under the same set of conditions, lost over 80% by weight of its original iron content after about 100 hours of use.

Another distinguishing feature of the solid solution catalysts of the invention is that the catalysts can be regenerated. This is accomplished by heat treating the solid solution catalyst by firing the catalyst at about 1200° C. or above to redistribute the iron cations to replace those lost from the active sites. The reactivation of the solid solution catalyst is not merely a reoxidation of a reduced catalyst for heating in pure oxygen at 550° C. for two hours does not restore activity.

Solid solution catalyst containing iron cations can be of different types. The iron exists as ferric ($Fe^{+3}$) and/or ferrous ($Fe^{+2}$) ions. The ferric ion is the active ion in the catalyst. However, as the ferrous ion can oxidize to a ferric ion in the process, the use of solid solution catalysts containing ferrous ions are within the scope of the invention.

One type of solid solution consists of iron ions substituted for host lattice ions wherein the iron ion(s) has a different oxidation state than that of the host lattice ion. An example of such a solid solution is $Zn(Ti_x^{+4}Fe_{2-2x}Fe_x^{+2})O_4$ wherein x is from 0 to 1. The iron, zinc, and titanium ions exist in an orderly arrangement, and the catalyst exhibits a single phase X-ray diffraction pattern. Another such solid solution catalyst is $(Al_{2-2x}^{+3}Fe_x^{+2}Ti_x^{+4})O_3$ wherein x is greater than 0 and up to 1. The iron, titanium and aluminum ions exist in an orderly arrangement, and the catalyst exhibits a single phase X-ray diffraction pattern. Other solid solution catalysts where the substituting iron ion(s) has an oxidation state different from that of the host lattice ion(s) exist.

A second type of solid solution containing iron cations is that wherein there is direct substitution of iron ions for host lattice ions wherein both ions have common oxidation states. An example of this type of catalyst is $(Fe_x^{+3}M_{2-x}^{+3})O_3$ wherein x is greater than 0 and less than 2, and M is a metal such as Al or Cr. As the ferric +3 ion is greater in size than an aluminum +3 ion, the solubility of the ferric ion in aluminum oxide is somewhat limited. Hence, the solid solution catalysts wherein M is aluminum encompass materials of the formula wherein x has a practical upper limit of about 0.15.

The solid solution catalysts of the invention are the type containing iron cations wherein there is direct substitution of iron ions for host lattice ions wherein both ions have the same or common oxidation state. Examples of these catalysts are a solid solution catalyst of ferric ion in alpha-aluminum oxide ($\alpha$-$Al_2O_3$) or in alphachromium oxide ($\alpha$-$Cr_2O_3$). The basic solid solution catalyst of iron cations in $\alpha$-$Al_2O_3$ or $\alpha$-$Cr_2O_3$ can contain other metal ions such as potassium (as the oxide), barium (as the oxide), Ce, and Ag (all as the oxides). Hence, other examples of solid solution catalysts of the invention which were prepared are iron in $K_2O.11Al_2O_3$ (or the iron in $\beta$-$Al_2O_3$ solid solution), iron in $BaO.6Al_2O_3$ (or the iron in $BaAl_{12}O_{19}$ solid solution), and iron in $Ba_{0.50}Ce_{0.17}Ag_{0.33}Al_{12}O_{19}$ (wherein Ce and Ag are in partial replacement of Ba).

Solid Solution Catalyst Identification and Characterization

The solid solution catalysts of the invention contain iron cations in specific host lattices and have X-ray diffraction patterns characteristic of the host lattice material. Solid solutions are known to exist (see C. S.

Barrett, *Structure of Metals, Crystallographic Methods, Principles, and Data,* 2nd Ed., McGraw-Hill Book Co., Inc. N.Y., N.Y. (1952), at pages 220 et seq.); V. L. Moruzzi et al, Phase Equilibria in the System $La_2O_3$-Iron Oxide in Air, J. Amer. Chem. Soc., Vol. 43, No. 7 (1960), pages 367–372; and Carman et al, Electron Spin Resonance of α-Chromia-Alumina Solid Solutions, J. Physical Chem., Vol. 72 (1968), pages 2562–2566).

The catalyst is first identified and characterized by analyzing it to determine what elements it contains. This can be done using well known techniques such as chemical analysis, atomic absorption spectroscopy, X-ray fluorescence spectroscopy, and optical microscopy. For example, the solid solution catalyst of iron in alpha-aluminum oxide would show iron, aluminum, and oxygen to be present in the catalyst. The presence and quantity of iron in the catalyst can be readily determined using a standard method of chemical analysis such as the dichromate method for the determination of iron. The amount of iron in the solid solution catalysts is limited by the solubility of the ions in the host lattice. The solid solution catalysts can contain from about 0.5 percent to 70 percent by weight and more preferably from about 1 percent to about 15 percent by weight of iron in the catalyst, the iron expressed as iron oxide.

The second step of identification and characterization involves running an X-ray diffraction scan on the catalyst. The X-ray diffraction scan will show a pattern of peaks, which peaks have positions and intensities distinctive of the crystalline phases which are present. The X-ray diffraction peak positions and intensities of the catalyst can be compared to peak positions and intensities of known crystalline phases that are published (in the ASTM Powder Diffraction File, for example), or that are experimentally obtained. For example, a catalyst comprised of iron oxide merely impregnated on or absorbed on aluminum oxide will have an X-ray diffraction pattern of peak positions showing the distinct peak positions and intensities of iron oxide and aluminum oxide crystalline phases.

In contrast, the X-ray diffraction pattern of a solid solution catalyst containing iron shows the positions of the X-ray diffraction peaks in the solid solution catalyst to be shifted from the peak positions in the X-ray diffraction pattern of the host lattice. The shift in peak positions may be accompanied by changes in the relative intensities of the peaks, but the intensity changes are generally small.

The shift in X-ray diffraction peak positions when solid solutions are formed results from the expansion (or contraction) of the dimensions of the unit cell of the crystalline phase of the host lattice. The dimensions of the unit cell of the host lattice are changed due to the substitution of iron cations for cations of the host lattice. If the cation is larger than the cation it displaces, the unit cell dimensions will increase in size to accommodate the larger cation. The amount of expansion (or contraction if the iron cation is smaller than the host lattice cation it displaces) of the unit cell dimensions can be determined by calculating the lattice parameters of the unit cell of the solid solution phase and comparing these lattice parameters to the lattice parameters of the unit cell of the host. A change in lattice parameters due to iron substitution in a crystalline host lattice is frequently in accordance with Vegard's law (see page 221 of the above-cited reference). Since a change in the lattice parameters causes a change in the X-ray diffraction peak positions, a comparison of the X-ray diffraction pattern of the catalyst and the pattern of the host lattice will show whether a solid solution catalyst has been prepared.

Alternately, a more accurate method of confirming the preparation of a solid solution catalyst is to experimentally run X-ray diffraction scans of the prepared catalyst and of the host lattice and then calculate the lattice parameters of each. If the values obtained for the lattice parameters of the catalyst and host lattice are different, a solid solution catalyst has been prepared. If the geometry and dimensions (lattice parameters) of the unit cell of the host lattice is not known, it can be determined using established methods for indexing and interpreting X-ray diffraction patterns (see L. V. Azaroff and M. J. Buerger, *The Powder Method In X-Ray Crystallography,* McGraw-Hill Book Co., Inc., N.Y., N.Y. (1958), chapters 6 to 13). The high $2\theta$ values (where $\theta$ is the Bragg angle) are normally used to calculate the lattice parameters.

In summary, the solid solution catalysts of the invention can be identified and characterized by (1) the presence of iron in the catalyst, and (2) the X-ray diffraction pattern of the catalyst. The iron is present as cations substituted in the host lattice for cations of the host lattice. The iron content can be measured using standard analysis techniques. The X-ray diffraction pattern of the solid solution catalyst will exhibit peak positions characteristic of the host lattice but shifted due to the presence of the iron cations in the host lattice. Lattice parameters calculated for the host lattice and the solid solution catalyst will differ. The X-ray diffraction pattern of the solid solution catalysts of the invention can exhibit extraneous peaks in the pattern due to formation of crystalline compounds other than the solid solution catalyst itself. For example, in preparing the iron in beta-alumina solid solution catalyst, the host lattice contains potassium, and $K_2O$ is formed and peaks due to the presence of $K_2O$ are seen in the X-ray diffraction pattern.

Preparation of Solid Solution Catalysts

The solid solution catalysts used in the Examples were prepared by first impregnating a host lattice precursor with an iron salt that yields the oxide upon heating, then heating the impregnated host lattice precursor to about 550° C. followed by heating to 1200° C. or more. The first heating converts the salts to oxides, and initiates conversion of the host lattice precursor to the host lattice. The second heating completes the formation of the host lattice and produces a rearrangement of the metal atoms between the metal ions in the host lattice and the iron ions. The catalyst prepared is a solid solution catalyst containing iron and having a distinctive X-ray diffraction pattern.

The solid solution catalyst can be prepared in other different ways. Another method is to physically admix iron oxide and the host lattice material and heat the mix to above about 1100° C. to allow dissolution and substitution of the iron ions for those of the host lattice, and formation of the stabilized catalyst. Heating conditions can vary for the nature of the host lattice employed, but are above about 1100° C.

A third method of preparation is to use the socalled sol-gel process wherein an iron salt and a salt precursor of the host lattice are mixed together as solutions and a base is added to coprecipitate out a mixture of the corresponding hydrated oxides. For example, ferric nitrate and aluminum nitrate can be dissolved in water and ammonium hydroxide added to the solution to coprecipitate a mixture of hydrated iron and aluminum oxides. The mix is then heated to above about 1100° C. to perfect dissolution and substitution of the iron ions for aluminum ions.

A fourth method is to dissolve an iron salt in a solvent such as water or ethanol and use the solution to impregnate the host lattice, then dry and heat the mix to above about 1100° C. to cause the metal salt to decompose upon heating to yield the oxide and to substitute the iron ions for those of the host lattice.

In all of these methods a metal oxide precursor can be used in place of the metal oxide per se. The precursor, which is typically a salt of the metal, decomposes on heating to yield the oxide form of the metal. Examples of iron oxide precursors are iron chloride, iron sulfate, iron formate, iron oxalate, iron citrate, iron nitrate, and the like.

The exact preparation of an iron in $\alpha$-$Al_2O_3$ solid solution catalyst is shown in the following example. Alumina trihydrate is used as the host lattice precursor, and an alcohol solution of ferric nitrate is used as the impregnating solution. 551 grams of alumina trihydrate ($Al_2O_3 \cdot 3H_2O$), sold commercially as Alcoa C-31, was placed into a porcelain dish. A solution of 76 grams of ferric nitrate, $Fe(NO_3)_3 \cdot 9H_2O$ dissolved in 250 milliliters of absolute ethanol was added to the alumina trihydrate in the dish and the mix stirred as it was heated to evaporate the ethanol. The impregnated material was then heated in air for 16 hours at 550° C. to dehydrate the alumina trihydrate to aluminum oxide and to decompose the ferric nitrate to ferric oxide. The impregnated aluminum oxide was passed through an 80 mesh screen and then placed into a platinum/rhodium crucible and heated in air for 16 hours at 1200° C. The catalyst obtained was sieved through screens and the portion passing through 80 mesh and held on 200 mesh was used for oxychlorination experiments.

The prepared catalyst was a solid solution catalyst of about 4% by weight of iron, expressed as the ferric oxide, in $\alpha$-aluminum oxide (iron in $\alpha$-$Al_2O_3$). The X-ray diffraction pattern of the solid solution catalyst exhibited a 0210 peak at 88.929° $2\theta$ and a 134 peak at 91.079° $2\theta$. The $\alpha$-$Al_2O_3$ host lattice exhibited its 0210 peak at 89.031° $2\theta$ and its 134 peak at 91.211° $2\theta$. Hence, the peak positions of the catalyst had shifted due to the presence of the iron cations in the aluminum oxide host lattice. The interplanar spacing between the planes in the crystalline lattice represented by the 0210 and 134 peak positions increased, going from a "d" value of 1.0986 Å for $\alpha$-$Al_2O_3$ to 1.0996 Å for the catalyst for the 0210 peak, and from 1.0780 Å to 1.0792 Å for the 134 peak. The lattice parameters calculated for the $\alpha$-$Al_2O_3$ were: "a" value=4.758 Å and "c" value=12.986 Å, while the lattice parameters for the solid solution catalyst were: "a" value=4.763 Å and "c" value=12.997 Å. The lattice parameters of this solid solution catalyst are larger than those of the $\alpha$-$Al_2O_3$ host lattice due to the substitution of the larger iron cations for aluminum cations in the host lattice.

Solid solution catalysts of iron cations in $\alpha$-$Al_2O_3$ were also prepared using a larger amount of ferric nitrate in solution to yield a solid solution catalyst having about 11% by weight of iron, expressed as $Fe_2O_3$, in the $\alpha$-$Al_2O_3$ host lattice. Likewise, other metal compounds which yield iron oxide on heating can be used in solution with other host lattices such as $K_2O \cdot 11\ Al_2O_3$ ($\beta$-$Al_2O_3$) and $BaO \cdot 6\ Al_2O_3$ ($BaAl_{12}O_{19}$).

The solid solution catalysts of the invention can be used in the process in the form of a fixed bed, a fluidized bed, on a fixed support, on a fluidized support, or in a number of ways well known to the art. Although in the examples the process used is a fluidized bed process, it is understood that other well known techniques can be employed. The following Examples are given to further illustrate the invention.

EXAMPLES

Oxychlorination Process

Solid solution catalysts of the invention were used in an oxychlorination process to react ethane to vinyl chloride. The reactions were conducted in a fluid bed reactor wherein the ethane, oxygen used in the form of air, and anhydrous HCl were premixed at a set molar ratio of reactants and the mixture fed into a heated reactor near the bottom. The catalyst was of a particle size (particles passing between 80 mesh and 200 mesh screens) and the feed rate selected to suspend the catalyst particles in the gas stream during the reaction. Contact times were from about 5 seconds to about 10 seconds. Products were withdrawn from the top of the reactor as gases, scrubbed with water and analyzed using a gas chromatograph. The process was run as a continuous process for times of 1 hour up to 140 hours per run.

The following examples detail experiments conducted using various mole ratios of reactants, various temperatures and times of reaction, and different solid solution catalysts.

EXAMPLE I

Experiments were conducted to compare ethane conversion, yield of vinyl chloride, and iron loss between a solid solution catalyst of this invention and a catalyst prepared by a standard method. The solid solution catalyst used was the iron in $\alpha$-$Al_2O_3$ solid solution catalyst prepared in the detailed procedure given above, and consisted of a solid solution of 4% by weight of iron, expressed as $Fe_2O_3$, in $\alpha$-$Al_2O_3$. The other standard catalyst employed in the comparison was prepared by impregnating $\alpha$-aluminum oxide with a solution of ferric nitrate, drying the mix, and then heating the mix for 16 hours at 550° C. to dehydrate the aluminatrihydrate and to decompose the ferric nitrate to ferric oxide. The preparation is the same as disclosed in the preparation of the solid solution catalyst except that no heating to 1200° C. was done.

The reactants were fed into the reactor at a mix of 1 mole ethane/1 mole of oxygen (as air)/4 moles of anhydrous hydrogen chloride. Contact time throughout the runs ranged from 5.7 to 7.8 seconds. Temperature of reaction was 550° C. Results are given in the following tables.

| Time (Hrs.) | Iron in $\alpha$-$Al_2O_3$ Solid Solution Catalyst | |
|---|---|---|
| | Mole % Conversion of Ethane | % Yield of Vinyl Chloride |
| 2 | 97.8 | 32.1 |
| 5 | 98.2 | 33.4 |
| 26 | 97.8 | 34.1 |
| 48 | 98.2 | 33.6 |
| 84 | 97.9 | 34.5 |
| 102 | 91.8 | 24.2 |
| 107 | 93.6 | 23.1 |

| Time (Hrs.) | Comparative Catalyst | |
|---|---|---|
| | Mole % Conversion of Ethane | % Yield of Vinyl Chloride |
| 1 | 99.0 | 23.8 |
| 5 | 98.2 | 26.8 |
| 31 | 99.2 | 26.9 |
| 55 | 99.2 | 28.6 |
| 62 | 98.4 | 31.0 |
| 99 | 97.4 | 29.6 |
| 109 | 99.0 | 27.7 |
| 119 | 98.8 | 24.2 |
| 141 | 97.6 | 17.5 |

The data show that the solid solution catalyst of the invention and the comparative catalyst are somewhat comparable in mole % conversion of ethane. However, the greater activity of the solid solution catalyst is demonstrated by the higher yields of vinyl chloride.

Another major difference between the two catalysts appears in the iron loss sustained by each catalyst. Results are reported in the following table. Iron content was determined using the dichromate process for the determination of iron.

| Time (Hrs.) | Percent Iron Retained | |
|---|---|---|
| | Solid Solution | Comparative |
| 0 | 100 | 100 |
| 26 | 97.1 | — |
| 28 | — | 67.1 |
| 48 | 94.9 | — |
| 51 | — | 43.6 |
| 83 | 86.9 | — |
| 101 | — | 15.0 |
| 107 | 85.4 | — |

The data show that after about 100 hours of reaction time, the solid solution catalyst lost only about 15% by weight of its initial iron content, while the other standard catalyst lost about 85% by weight of its iron.

The solid solution catalysts of the invention can be regenerated when they show a loss in activity to give conversions and yields comparable to original values. The comparative catalyst, having lost most of its iron when its activity decreased, could not be regenerated. The conversion and yield data in the preceding tables show that at about 15% loss of iron in the solid solution catalyst (at about 100 hours), the activity of the catalyst decreased. The following experiment shows the regeneration of the solid solution catalyst. The solid solution catalyst of 4% by weight of iron, expressed as $Fe_2O_3$, in $\alpha$-$Al_2O_3$ was first heated to 550° C. for two hours in pure oxygen and then evaluated for its activity. No increase in activity was observed. This demonstrates that the regeneration is not simply a reoxidation process. The solid solution catalyst was then heated to 1300° C. for 20 hours and again evaluated for its activity. The catalyst activity was excellent and comparable to its original activity. Data are given in the following table.

| | Solid Solution Catalyst | |
|---|---|---|
| | Mole % Conversion of Ethane | % Yield of Vinyl Chloride |
| Original Catalyst | | |
| at 2 hours | 97.8 | 32.1 |
| at 5 hours | 98.2 | 33.4 |
| at 107 hours | 93.6 | 23.1 |
| Oxidation Treated | | |
| at 1.25 hours | 90.9 | 21.9 |
| Heat Treated (1300° C.) | | |
| at 5 hours | 98.4 | 34.0 |

EXAMPLE II

A solid solution catalyst of 4% by weight of iron, expressed as $Fe_2O_3$, in $\alpha$-$Al_2O_3$ (the same as that employed in Example I) was used in the oxychlorination of ethane. The process herein is similar to that of Example I but for the mole ratio of reactants. The feed stream comprised 1 mole of ethane/1 mole of oxygen (as air)/2 moles of anhydrous hydrogen chloride rather than 4 moles of HCl as in the previous example. Contact time was 6.5 to 7.1 seconds. The use of a lower ratio and amount of HCl in the process results in slightly lower conversions of ethane, lower yields of vinyl chloride, higher yields of ethylene, and less iron loss from the catalyst (about one-half the iron loss shown in the previous example). The following table shows the data obtained.

| Time (Hours) | Weight % Iron Loss | Mole % Conversion of Ethane | % Yield of | |
|---|---|---|---|---|
| | | | Vinyl Chloride | Ethylene |
| 17 | — | 94.9 | 21.6 | 50.2 |
| 20 | — | 94.8 | 21.9 | 49.4 |
| 41 | — | 94.8 | 21.0 | 51.1 |
| 47 | 3.0 | — | — | — |
| 67 | — | 94.4 | 22.1 | 47.1 |
| 94 | — | 94.2 | 21.9 | 46.5 |
| 107 | 8.7 | 94.7 | 20.9 | 52.5 |
| 115 | — | 94.4 | 20.6 | 51.3 |
| 139 | — | 91.8 | 18.1 | 51.0 |

EXAMPLE III

A solid solution catalyst of 11% by weight of iron, expressed as $Fe_2O_3$, in $\alpha$-$Al_2O_3$ prepared as above was evaluated in an oxychlorination process similar to that in Example II (i.e., a 1/1/2 mole ratio of ethane/oxygen/HCl and a contact time of 6.7 to 7.1 seconds). The higher level of iron in the catalyst resulted in somewhat higher conversions and yields. After 140 hours of reaction time, the solid solution catalyst was regenerated and reactivated by heat treating it at 1300° C.

| Time (Hrs.) | Mole % Conversion of Ethane | % Yield of | |
|---|---|---|---|
| | | Vinyl Chloride | Ethylene |
| 1 | 93.4 | 26.6 | 48.9 |
| 20 | 94.5 | 26.1 | 48.4 |
| 46 | 95.9 | 26.6 | 50.6 |
| 69 | 95.6 | 26.7 | 50.2 |
| 89 | 95.4 | 25.6 | 50.8 |
| 100 | 97.9 | 22.4 | 61.1 |
| 116 | 97.8 | 19.4 | 60.7 |
| 140 | 98.4 | 19.0 | 59.1 |
| 2[a] | 99.0 | 24.7 | 55.6 |

[a]Catalyst heat treated at 1300° C. to regenerate it

EXAMPLE IV

A solid solution catalyst of $Fe^{3+}$ ions substituted for $Al^{3+}$ ions in a $\beta$-$Al_2O_3$ host lattice was prepared. A mixture of aluminum trihydrate and potassium carbonate was impregnated with an ethanol solution of ferric nitrate. The mix was dried, ground, and heated at 560° C. for 16 hours to dehydrate the aluminum trihydrate, and decompose the ferric nitrate to ferric oxide. The material was then heated at 1200° C. for 16 hours to decompose the potassium carbonate to potassium oxide and to yield the iron in $\beta$-$Al_2O_3$ solid solution catalyst which can be expressed as ($K_2O.11\ Fe_2O_3$ in $K_2O.11\ Al_2O_3$). The final catalyst composition had a concentration of iron, expressed as the oxide, of about 4% by weight.

The iron in $\beta$-$Al_2O_3$ solid solution catalyst was evaluated in an oxychlorination process using ethane. The data given in the following table was generated in a continuous, fluid bed reactor process wherein the ethane/oxygen (as air)/HCl mole ratio was 1/1/4, temperature of reaction was 500° C., and contact time was about 7 seconds.

| Time (Hrs.) | $\beta$-$Al_2O_3$ Solid Solution Catalyst | | |
|---|---|---|---|
| | % Mole Conversion of Ethane | % Yield of Vinyl Chloride | Ethylene |
| 6 | 96.4 | 38.5 | 26.3 |
| 24 | 97.6 | 41.4 | 25.3 |
| 32 | 96.6 | 41.2 | 23.8 |
| 69 | 96.2 | 38.4 | 27.7 |
| 74 | 92.8 | 33.7 | 23.4 |
| 88 | 94.5 | 31.4 | 28.8 |
| 100 | 91.3 | 25.3 | 26.1 |

The data show that good mole percent conversions of ethane and high yields of vinyl chloride and ethylene are obtained using the $\beta$-$Al_2O_3$ solid solution catalyst containing iron cations. The yields of vinyl chloride are higher and yields of ethylene are lower than those obtained using the iron in $\alpha$-$Al_2O_3$ solid solution catalyst (see Examples I and II).

EXAMPLE V

Using the $\beta$-$Al_2O_3$ solid solution catalyst prepared in Example IV, a series of oxychlorination experiments were run varying temperature of reaction and mole ratios of oxygen and HCl in the feed mixture. Contact times varied from about 6 to about 10 seconds. The data listed below were obtained from a continuous, fluid bed reactor process wherein temperature or molar feed ratio was varied and the process allowed to reach a steady-state before measuring conversion and yields.

| Sample | Reaction Temperature (°C.) | Ethane/$O_2$/HCl Mole Ratio | Mole % Conversion of Ethane | % Yield of Vinyl Chloride | % Yield of Ethylene | Ethylene Dichloride | Ethyl Chloride | Total Combined Yield, Percent |
|---|---|---|---|---|---|---|---|---|
| 1 | 425 | 1/1/4 | 66.1 | 12.0 | 9.3 | 6.6 | 47.2 | 75.1 |
| 2 | 450 | 1/1/4 | 81.3 | 19.9 | 13.5 | 6.4 | 34.1 | 73.9 |
| 3 | 475 | 1/1/4 | 94.8 | 35.2 | 23.6 | 2.3 | 15.1 | 76.2 |
| 4 | 500 | 1/1/4 | 96.4 | 38.5 | 26.3 | 5.4 | 9.9 | 80.1 |
| 5 | 550 | 1/1/4 | 98.6 | 38.0 | 34.1 | 3.5 | 3.4 | 79.0 |
| 6 | 500 | 1/1/4 | 97.6 | 41.4 | 25.3 | 4.1 | 7.9 | 78.7 |
| 7 | 500 | 1/1/3 | 96.5 | 37.6 | 20.1 | 3.1 | 10.4 | 71.1 |
| 8 | 500 | 1/1/2 | 92.7 | 26.0 | 25.0 | 4.5 | 19.8 | 75.3 |
| 9 | 500 | 1/0.8/4 | 93.6 | 36.4 | 29.8 | 4.5 | 15.5 | 86.2 |
| 10 | 500 | 1/0.8/3 | 91.1 | 30.5 | 32.5 | 4.6 | 20.9 | 88.5 |
| 11 | 500 | 1/0.8/2 | 89.5 | 27.8 | 29.9 | 5.0 | 23.7 | 86.4 |
| 12 | 500 | 1/0.7/4 | 98.1 | 31.3 | 31.3 | 5.2 | 21.7 | 89.5 |
| 13 | 500 | 1/0.7/3 | 88.7 | 31.1 | 33.6 | 3.9 | 19.2 | 87.8 |
| 14 | 500 | 1/0.7/2 | 80.1 | 23.3 | 34.2 | 2.8 | 26.2 | 86.5 |

The data show that increasing temperature increases mole percent conversion and yields of vinyl chloride and ethylene. A minimum temperature of about 400° C. is necessary to produce minimal yields of vinyl chloride. A decreasing molar HCl ratio resulted in a decreased mole percent conversion of ethane, decreased vinyl chloride yield, and an increased ethyl chloride yield, while ethylene dichloride and ethylene yield were relatively unaffected. A decreasing molar oxygen ratio decreases mole percent conversion of ethane and decreases vinyl chloride yield, while ethylene and ethyl chloride yields increase. Total combined yield is relatively unaffected by the process changes, except for a noted increase in combined yield as the oxygen ratio decreased.

EXAMPLE VI

A solid solution catalyst was prepared wherein $Fe^{3+}$ ions are substituted for $Al^{3+}$ ions in a host lattice of barium aluminate ($BaAl_{12}O_{19}$). The catalyst was prepared by impregnating alumina trihydrate with a water solution of ferric nitrate and barium nitrate, drying the mix, and heating at 660° C. for 16 hours to dehydrate the alumina trihydrate and decompose the nitrates into oxides. The material was then heated at 1350° C. for 16 hours to produce a solid solution catalyst which can be formulated as a solid solution of $BaFe_{12}O_{19}$ in $BaAl_{12}O_{19}$. Two catalysts containing 3.83% by weight and 7.66% by weight $BaFe_{12}O_{19}$ in $BaAl_{12}O_{19}$ were prepared.

The barium aluminate solid solution catalysts were evaluated as oxychlorination catalysts following the procedures previously given. Mole ratio of reactants was 1 ethane/1 oxygen/4 HCl, temperature of reaction was 550° C., and contact time was 6.6 to 7.1 seconds. In contrast to the use of the iron in $\alpha$-$Al_2O_3$ solid solution catalyst of Example I, the use of the barium aluminate solid solution catalysts resulted in a higher yield of ethylene and a lower yield of vinyl chloride. Mole percent conversion of ethane was comparable using both catalysts.

| Time (Hrs.) | Mole % Conversion of Ethane | % Yield of Vinyl Chloride | Ethylene |
|---|---|---|---|
| 3.83% BaFe$_{12}$O$_{19}$ in BaAl$_{12}$O$_{19}$ | | | |
| 4 | 97.1 | 17.0 | 59.6 |
| 21 | 96.6 | 17.3 | 59.8 |
| 7.66% BaFe$_{12}$O$_{19}$ in BaAl$_{12}$O$_{19}$ | | | |
| 1 | 99.2 | 20.7 | 59.2 |
| 29 | 97.0 | 19.1 | 58.9 |
| 49 | 94.4 | 17.6 | 59.3 |
| 61 | 93.5 | 17.2 | 59.9 |
| 88 | 90.5 | 15.4 | 62.1 |
| 108 | 88.8 | 15.5 | 61.0 |

EXAMPLE VII

Following the catalyst preparation procedure given in Example VI, a solid solution catalyst was prepared containing aluminum, iron, barium, cesium, and silver ions. Alumina trihydrate was impregnated with a water solution of ferric nitrate, barium nitrate, cesium nitrate, and silver nitrate. The mix was dried, heated at 660° C. for 16 hours, and then heated at 1350° C. for 16 hours. The solid solution catalyst prepared can be formulated as Ba$_{0.50}$Ce$_{0.17}$Ag$_{0.33}$Fe$_{0.65}$Al$_{11.35}$O$_{19}$. Its structure is similar to that of the catalyst prepared in Example VI, the difference being partial replacement of Ba ions by a combination of Ce and Ag ions.

The solid solution catalyst was evaluated as an oxychlorination catalyst. Process and reaction conditions employed were the same as in Example VI. The use of the complex barium aluminate solid solution catalyst resulted in slightly higher mole percent conversions of ethane and higher yields of vinyl chloride in comparison with the barium aluminate solid solution catalyst of Example VI.

| Time (Hrs.) | Mole % Conversion of Ethane | % Yield of Vinyl Chloride | Ethylene |
|---|---|---|---|
| 1 | 98.6 | 22.9 | 58.5 |
| 7 | 99.3 | 24.3 | 56.7 |
| 31 | 99.6 | 22.8 | 58.3 |
| 49 | 99.3 | 19.3 | 61.2 |

We claim:

1. In the process of oxychlorination of ethane to prepare ethylene, vinyl chloride, and other chlorinated hydrocarbons, the improvement comprising the use of, as a catalyst, a solid solution catalyst consisting of iron cations in a host lattice of $\alpha$-Al$_2$O$_3$ or $\beta$-Al$_2$O$_3$, said catalyst having an iron content from about 1 percent to about 15 percent by weight, expressed as the oxide, prepared by employing a calcinating step at temperatures above about 1100° C., and having an X-ray diffraction pattern having peak positions in the pattern different than that of its host lattice.

2. In the process of oxychlorination of an alkane of 1 to about 12 carbon atoms at a temperature from about 400° C. to about 650° C. wherein the alkane, oxygen, and hydrogen chloride are employed at a mole ratio of 1 mole of alkane to 0.1 to 10 moles of hydrogen chloride to 0.1 to 1.5 moles of oxygen, the improvement comprising the use of, as a catalyst, a solid solution catalyst consisting of iron cations in a host lattice of $\alpha$-Al$_2$O$_3$ or $\beta$-Al$_2$O$_3$, said catalyst having an iron content from about 1 percent to about 15 percent by weight, expressed as the oxide, prepared by employing a calcinating step at temperatures above about 1100° C., and having an X-ray diffraction pattern having peak positions in the pattern different than that of its host lattice.

3. A process of claim 2 wherein the alkane employed has 2 to about 6 carbon atoms in the molecule.

* * * * *